United States Patent [19]

Erath

[11] Patent Number: 4,694,174

[45] Date of Patent: Sep. 15, 1987

[54] INFRARED GAS DETECTOR

[75] Inventor: Louis W. Erath, Abbeville, La.

[73] Assignee: Gas Alarm Service, Inc., Abbeville, La.

[21] Appl. No.: 782,516

[22] Filed: Oct. 1, 1985

[51] Int. Cl.$^4$ ............................................. G01N 21/61
[52] U.S. Cl. ..................................... 250/345; 250/343
[58] Field of Search ............... 250/345, 346, 343, 339; 364/572, 574; 328/165

[56] References Cited

U.S. PATENT DOCUMENTS

| | | | |
|---|---|---|---|
| 3,916,179 | 10/1975 | Cuzzo | 364/835 |
| 3,968,370 | 7/1976 | Luft | 250/344 |
| 4,387,438 | 6/1983 | Lucich et al. | 364/574 |
| 4,409,069 | 10/1983 | Luft | 204/1 T |
| 4,467,435 | 8/1984 | Warnke et al. | 364/497 |

OTHER PUBLICATIONS

Beckman Instrument Company Catalog No. 4201B, 1980.
Horiba Instruments Co. Instruction Manual for Model PIR-2000 Infrared Gas Detector, Mar., 1982.

Primary Examiner—Janice A. Howell
Assistant Examiner—Constantine Hannaher
Attorney, Agent, or Firm—Arnold, White & Durkee

[57] ABSTRACT

An apparatus and method for detecting gas concentration using an infrared absorption gas detector. Noise due to vibration is substantially reduced by integrating the voltage produced by the gas detector with an integrator having an adjustable time constant. The time constant is adjusted to a long value during times when the gas concentration is remaining relatively constant. When the gas concentration is changing substantially, the time constant is adjusted to a relatively short value to allow the output of the integrator to better follow the changes.

15 Claims, 8 Drawing Figures

INFRARED GAS DETECTOR

DESCRIPTION OF THE PRIOR ART

1. Field of the Invention

This invention relates to the detection of the presence of a gas by the measurement of infrared absorption. More particularly, this invention relates to an improved apparatus and method for infrared absorption gas detection which overcomes inherent sensitivity to noise and vibration found in prior art measurement devices.

2. Background Art

The technology of gas detection finds application in a wide range of scientific and technical disciplines. For example, gas detectors are commonly used to determine the component gasses in automobile exhaust so as to measure the effectiveness of pollution control devices. Gas detection devices are also used for a variety of applications in oilwell drilling technology.

One important oil technology application is the detection of gas in drilling mud. During drilling, specially compounded muds are forced down into the well under pressure to counter subsurface pressures and thus prevent well blowout. As the drilling proceeds, gases found below the surface permeates the drilling mud. Pursuant to U.S. Coast Guard requirements, drilling mud used on off-shore drilling platforms is regularly brought to the surface and monitored to detect the presence of gas content of the mud as an indicator of the dangers of well blowout.

It is also important to monitor the presence of methane which may be emitted from the well during drilling. Quantities of methane mixed with air form an explosive mixture. Detection of the presence of methane encountered while drilling is thus an important safety measure.

One device commonly used for the detection of methane and other hydrocarbon gasses is the platinum wire detector. Samples of well gas are burned in the presence of a platinum wire through which a current is passed. The heat of combustion changes the resistance of the platinum wire which results in a change in the flow of current in the wire. One disadvantage of this type of detector is that other gasses encountered in well drilling can contaminate the surface of the wire resulting in a loss of sensitivity of the detector. Also, the methane or other hydrocarbon must be mixed with a sufficient supply of oxygen to support combustion. A third disadvantage is that nonflammable gasses such as carbon dioxide are not detectable with this type of device.

A more satisfactory device is the Luft detector, an embodiment of which is shown in U.S. Pat. No. 3,968,370. The presence of a gas in an air sample is detected by measuring the absorption of infrared radiation by the air sample. One commercially available instrument utilizing an embodiment of the Luft detector is the Model 864 Infrared Analyzer manufactured by Beckman Instruments, Inc., of Fullerton, Calif. Another commercially available instrument comprising an embodiment of the Luft detector is the Model PIR-2000 Infrared Gas Analyzer manufactured by Horiba Instruments, Inc., of Irvine, Calif.

One common embodiment of the Luft detector comprises a sample chamber filled with an unknown gas mixture, a reference chamber filled with a reference gas, and a detection chamber. The detection chamber is partitioned by a flexible metal diaphragm into two detection zones, each zone being filled with a sample of the reference gas. The embodiment further comprises a pair of infrared energy sources. One source imparts a beam of infrared energy through the sample chamber and into one of the detection zones. The second source imparts a beam of infrared energy through the reference chamber and into the other detection zone. An optical chopper periodically interrupts the beams as they enter the detection chamber.

Gasses may be characterized by the particular wavelengths of infrared energy they absorb. Each of the two infrared beams is filtered so as to contain only those wavelengths absorbed by the reference gas. Thus, if the sample chamber contains only the reference gas, both infrared beams will have equal amounts of energy absorbed on their respective paths to the detection zones. Hence, the reference gas in each detection zone will be equally heated by infrared energy, and the pressure in each zone will be equal. However, if the sample chamber contains some gas other than the reference gas, differing amounts of energy will be absorbed from the two beams. The reference gas in one detection zone will be heated to a greater extent than that in other detection zone. A pressure differential will thus be created between the two detection zones which will cause deformation of the diaphragm.

Deformation of the diaphragm is detected by placing a metal plate close to the diaphragm so as to form a capacitor. As the diaphragm is deformed by the pressure differential, the capacitance of the capacitor changes. A D.C. voltage is applied to the series combination of a resistor and the diaphragm-plate capacitor. As the deformation of the diaphragm causes capacitance changes, a varying voltage substantially proportional to the capacitance change may be measured across the diaphragm plate capacitor.

The diaphragm must be light and flexible so as to be responsive to the range of pressure differentials encountered. Hence, it can be excessively sensitive to mechanical vibration. Extremely heavy vibration is encountered on drilling platforms due to machinery used in drilling. As a result, infrared absorption gas detection instruments have not been successfully used on drilling platforms. An improved signal processor is required which may detect variations of capacitance in the diaphragm-plate capacitor due to changes in the concentration of reference gas detected in the zone. Such a signal processor would be required to be relatively immune to variations in the capacitance caused by heavy vibration noise typically encountered in the drilling platform environment.

SUMMARY OF THE INVENTION

It is a general object of the invention to provide a method and apparatus for detecting those variations in capacitance of the diaphragm-plate capacitor responsive to gas concentration changes while being immune to those capacitance changes induced by vibratory noise. According to a general aspect of the invention, an electronic signal processor is presented which is suitable to process the varying voltage across the diaphragm-plate capacitor and which will be relatively insensitive to components of that voltage induced by mechanical vibration of the diaphragm. The signal processor comprises an electronic integrator with an adjustable time constant adapted to integrate the capacitor voltage so as to produce a signal substantially proportional to the concentration of the reference gas in the sample chamber of the Luft detector. The signal processor further comprises circuitry adapted to adjust the integrator's time constant responsive to the rate of change of the capacitor voltage. The signal processor further comprises display means adapted to display the output of the integrators as the concentration of reference gas in the sample chamber.

According to a more specific aspect of the invention, one embodiment of the invention additionally comprises an optical chopper adapted to interrupt the twin infrared beams of the Luft detector, and a synchronous demodulator adapted to detect and sample the chopped voltage appearing across the diaphragm-plate capacitor.

In another embodiment, a fast integrator is adapted to integrate the output of the synchronous demodulator. The rates of change of the outputs of the variable speed integrator and the fast integrator are compared so as to provide a basis for adjusting the time constant of the variable speed integrator.

In still another embodiment, the signal processor further comprises a noise inhibitor circuit which further improves the noise immunity of the signal processor.

Additionally, according to a general aspect of the invention, a method for detecting reference gas concentration using the Luft detector comprises the steps of producing a voltage substantially proportional to the deformation of the diaphragm, integrating the voltage in a variable speed integrator, and adjusting the time constant responsive to the rate of change of the gas concentration. According to a more specific aspect of the invention, the voltage is produced by a method comprising the steps of chopping the twin beams of the Luft detector at a preselected frequency and synchronously demodulating the voltage across the diaphragm-plate capacitor to produce the voltage substantially proportional to the concentration.

DESCRIPTION OF THE DRAWINGS

The following detailed description of the preferred embodiment of the invention may be better understood when read in conjunction with the accompanying drawings, wherein.

DESCRIPTION OF THE PREFERRED EMBODIMENT

A. D.C. Voltage is supplied through a resistor to the capacitor formed by the diaphragm and the plate spaced closely to it. As the diaphragm is deformed, both by pressure differential between the detection zones and by mechanical vibration, the voltage across the capacitor will vary proportional to the deformation. This varying voltage will have a periodic component resulting from the periodic interruption of the infrared beams by the rotating optical chopper. During the time the beams are interrupted, the pressure differential between the two detection zones will tend toward zero, causing the diaphragm to return to its rest position. When the beams are allowed to enter the detection zones once more, uneven heating of the gas in the respective zones will once more create a pressure differential and deform the diaphragm. The periodic component of the varying voltage will have a period of about 10 Hertz.

This varying voltage is sampled in a synchronous demodulator which produces the sampled version of the varying voltage as two bi-phase outputs. The bi-phase outputs are substantially equal in amplitude but are opposite in sign, making them electrical inversions of each other. In general, the noise content of each bi-phase signal will be expected to be somewhat different from that of the other bi-phase signal. The sampling rate of the synchronous demodulator is controlled by the optical chopper so that sampling will be in synchronism with the optical chopper. Noise in the capacitor voltage due to vibration will have an essentially random component as well as an essentially periodic component. The periodic component occurs in oilwell drilling operations due to the vibration caused by the drilling machinery and has a period of about 3 Hertz. Sampling at a constant periodic rate serves to overcome much of the essentially random noise but may set up beats or heterodyning with the periodic noise component. Reduction of the periodic noise may be effected by "wobulating" the speed of the optical chopper, that is, by varying the chopping frequency above and below the center frequency of 10 Hertz.

An electronic integrator responds to a sudden jump in input signal by gradually rising to a new level of output voltage. If the input voltage is suddenly increased from 0 volts to a value of V volts, the output voltage will be expressed as a function of time t by:

$$V_{out} = KV \exp(t/T)$$

where
K = low frequency gain
T = integration time constant
and
exp (·) is the exponential function A greater value of T will cause the exponential rise to require a longer time to complete. Although theoretically the rise takes infinite time, the rise is generally considered complete after a time duration equal to between 3T and 5T. An integrator with a relatively short time constant is said to be "faster" than one with a relatively longer time constant since the shorter time constant allows a faster rise time.

Passing a relatively low frequency signal contaminated with relatively high frequency noise through an electronic integrator may serve to eliminate much or all of the noise, provided the integrator's time constant is correctly chosen. If there is sufficient separation between the frequency components of the desired signal and that of the contaminating noise, selection of the time constant may be easy. The time constant is simply selected so that the integration can respond fast enough to the low frequency signal while being unable to respond fast enough to reproduce the noise components. When, however, the respective frequency bands of signal and noise are relatively closely spaced in the frequency spectrum, time constant selection may be more difficult. Under these circumstances, it may be impossible to select an optimum single value of time constant so that noise is eliminated without simultaneously filtering out some of the frequency components of the desired signal. This problem may be remidied by using an integrator with a time constant adjustable in response to certain characteristics of the signal to be integrated. In oilwell drilling applications, it is frequently necessary to monitor gas concentrations which rise from near zero to a maximum level in a few seconds, and which maintain that maximum from one to several minutes. A relatively fast integrator is required to monitor the rise in gas concentration while a much slower integration is needed to observe the longer period during which the maximum value occurs.

In an embodiment of the present invention, a variable speed integrator is adapted to integrate and filter one of the bi-phase outputs of the synchronous demodulator and drive a display, such as a calibrated gauge or digital meter, so as to indicate concentration of the reference gas in the gas detector's sample chamber. The second bi-phase signal is integrated in a fast integrator having a fixed time constant selected so as to pass some of the noise present in the second bi-phase signal. Circuitry is required which is adapted to comparing the respective rates of change of the outputs of the variable speed integrator and the fast integrator. This circuitry is preferably implemented with a summing integrator.

The outputs of the two integrators are additively combined and the sum integrated in the summing integrator. Since the bi-phase outputs are inverted versions of each other, the summing integrator produces an output approximately equal to the filtered difference of the first two integrator outputs. The output of the summing integrator will be near zero except during rapid increases or decreases in the concentration of reference gas in the sample chamber. The output of the fixed integrator will change relatively rapidly as the gas concentration changes. The variable speed integrator, adjusted to its longest time constant during periods of relatively no change in gas concentration, will change more slowly when gas concentration begins to change. When the difference between the output of the fixed integrator and the variable speed integrator exceeds a preselected threshold, the time constant of the variable speed integrator is reduced to allow the variable speed integrator to follow the gas concentration change.

Since the change in gas concentration may represent either an increase or a decrease, the output of the summing integrator may assume either a positive or negative value. An absolute value circuit is provided to produce a non-negative signal proportional to the magnitude of the summing integrator output. A time constant control circuit responsive to the absolute value circuit output serves to adjust the time constant of the variable speed integrator.

Thus, during periods of no change or relatively slow change in gas concentration, the variable speed integrator operates with a long time constant and passes virtually no noise which is present in the bi-phase signals. During periods in which a sufficiently large change in gas concentration occurs in a sufficiently short time interval, the variable speed integrator operates with a shorter time constant so as to more accurately reproduce this change.

Figure 1:
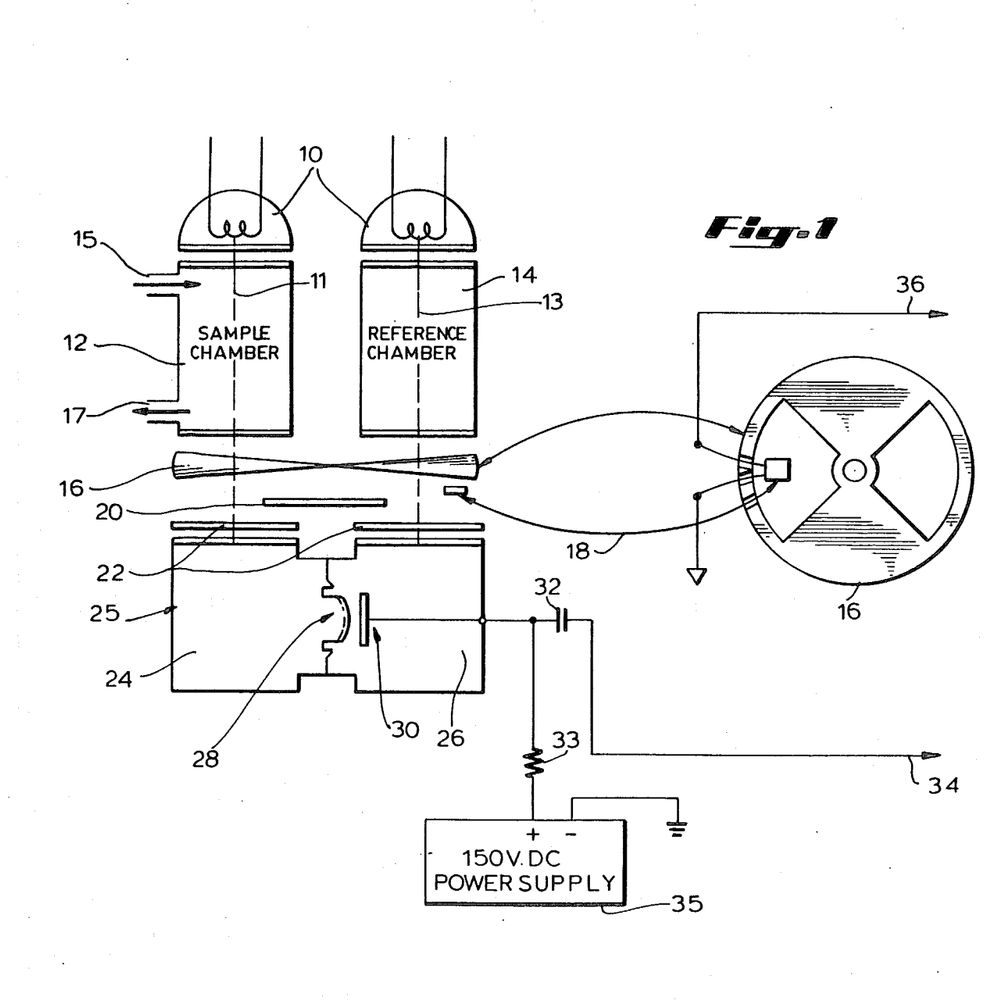
FIG. 1 shows an embodiment of the Luft detector.

Referring now to FIG. 1, infrared sources 10 direct infrared energy beams 11 and 13 into sample chamber 12 and reference chamber 14, respectively. A gas mixture of unknown composition is introduced into the sample chamber 12 through inlet 15 and flows out through outlet 17. Beam 11 passes through sample chamber 12 into a first detection zone 24 while beam 13 passes through reference chamber 14 into a second detection zone 26. Optical chopper 16, shown both in a top view as well as a cross-section view, is rotated so as to periodically interrupt beams 11 and 13. Infrared filters 22 are selected to pass only those wavelengths of lights absorbed by a reference gas to be detected. The reference chamber 14 and the detection zones 24 and 26 are filled with the reference gas.

Slicer 20 is opaque to infrared radiation and is adjustably positioned so as to balance infrared beams 11 and 13. It is desired to have equal amounts of infrared energy entering detection zones 24 and 26 when the sample chamber contains only a sample of the references gas. Slicer 20 would thus be adjusted during calibration of the system and would be held fixed during actual gas detection.

Diaphragm 28 is metallic and sufficiently flexible so as to respond to differences in pressure between zones 24 and 26. A metal plate 30 is placed sufficiently close to diaphragm 28 so as to form a capacitor. The capacitor so formed will have a capacitance approximately proportional to the spacing between diaphragm 28 and plate 30. Differences in pressure between zones 24 and 26 will cause deformation of diaphragm 28 so as to change this spacing.

Figure 2:
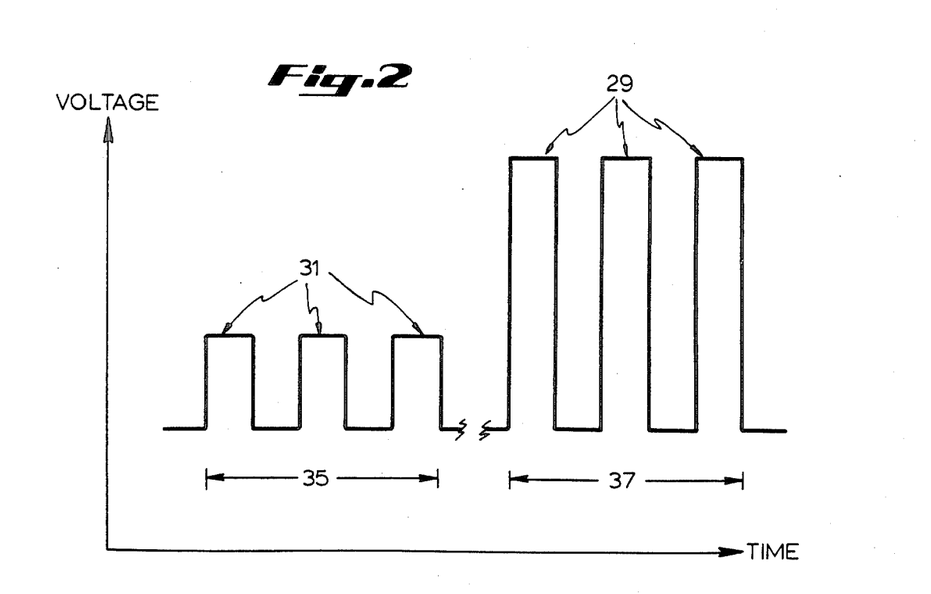
FIG. 2 shows the voltage waveforms measured across the diaphragm-plate capacitor.

When optical chopper 16 is oriented so as to interrupt beams 11 and 13, reference gas in zones 24 and 26 will have equal temperature and will thus have the same pressure. Rotation of optical chopper 16 to allow beams 11 and 13 to pass into detection zones 24 and 26 will cause infrared heating of the reference gas therein. Referring now to FIG. 2, the voltage measured across the capacitor formed by the diaphragm 28 and the plate 30 is seen to be essentially a square waveform with time. In interval 35, a lower gas concentration is being measured, while the gas concentration measured during interval 37 is higher. Voltage peaks 31 and 29 occur during the time the optical chopper is passing the beams 11 and 13. The voltage falls during the times between the peaks as the beams 11 and 13 are interrupted.

Capacitor 32 in FIG. 1 serves to block the large D.C. component of the voltage measured at plate 32 leaving only the varying part of the voltage to form gas detection output signal 34. Photodiode 18 receives a portion of beam 13 as it is passed by optical chopper 16 and produces photo diode output signal 36.

Photodiode 18 is an infrared sensitive semiconductor diode of a type well known and commercially available in the electronic art. Infrared radiation impinging upon photodiode 18 causes its conductivity to increase. Variations in the conductivity of photodiode 18 will be periodic as the beam 13 is periodically interrupted and these changes in conductivity will be sensed through photodiode output signal 36 by the synchronous demodulator 38 shown in FIG. 3.

Figure 3:
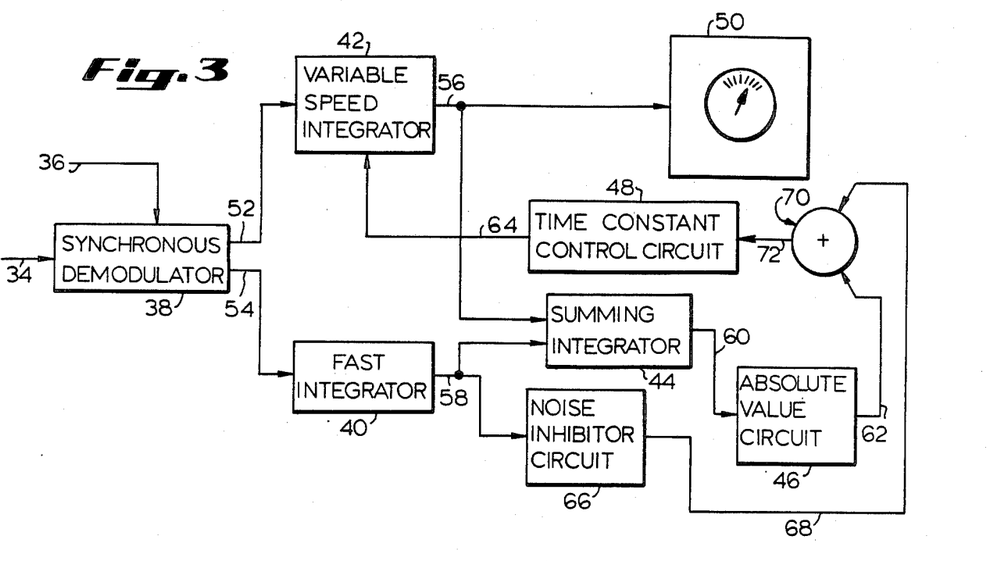
FIG. 3 shows a block diagram of the signal processor.

Referring now to FIG. 3, gas detector output signal 34 and photodiode output signal 36 are conducted into synchronous demodulator 38 wherein are produced bi-phase signals 52 and 54. Bi-phase signal 52 is conducted into variable speed integrator 42 where it is integrated to produce gas concentration signal 56. Gas concentration signal 56 is further conducted into display means 50 for display.

In a simple embodiment, display means 50 may simply be galvanometer type volt meter with calibrations on its dial indicating measured gas concentration in convenient units such as parts per million. A more sophisticated embodiment of the display means 50 would be a digital voltmeter similarly calibrated. Display means 50 may also be implemented using a chart recorder in which a moving pen is driven by gas concentration signal 56 so as to plot gas concentration as a function of time. Display means 50 may be implemented by any graphical or numerical display device capable of displaying the gas concentration in suitable units.

Bi-phase signal 54 is conducted into fast integrator 40 wherein is produced fast integrator output signal 58. The integrator 40 is referred to as fast in that its time constant is essentially equal to the lowest value of time constant assumed by the variable speed integrator. Fast integrator output signal 58 will generally contain a higher level of noise than gas concentration signal 56. Fast integrator output signal 58 is conducted into summing integrator 44 along with gas concentration signal 56. Summing integrator 44 additively combines signals 56 and 58 and integrates the sum to form summing integrator output signal 60. Absolute value circuit 46 produces output signal 62 which is a non-negative signal responsive to signal 60.

Noise inhibitor circuit 66 responds to fast integrator output signal 58 and produces an output signal 68 additively combined with absolute value output signal 62 in summing circuit 70. The resulting sum, signal 72, is conducted into time constant control circuit 48. The contributing of signals 68 and 62 to signal 72 are opposite in magnitude so that signal 72 is the algebraic sum of signals 68 and 62. Time constant control circuit 48 will send a time constant control signal 64 to variable speed integrator 64 responsive to the magnitude of signal 72.

Figure 4:
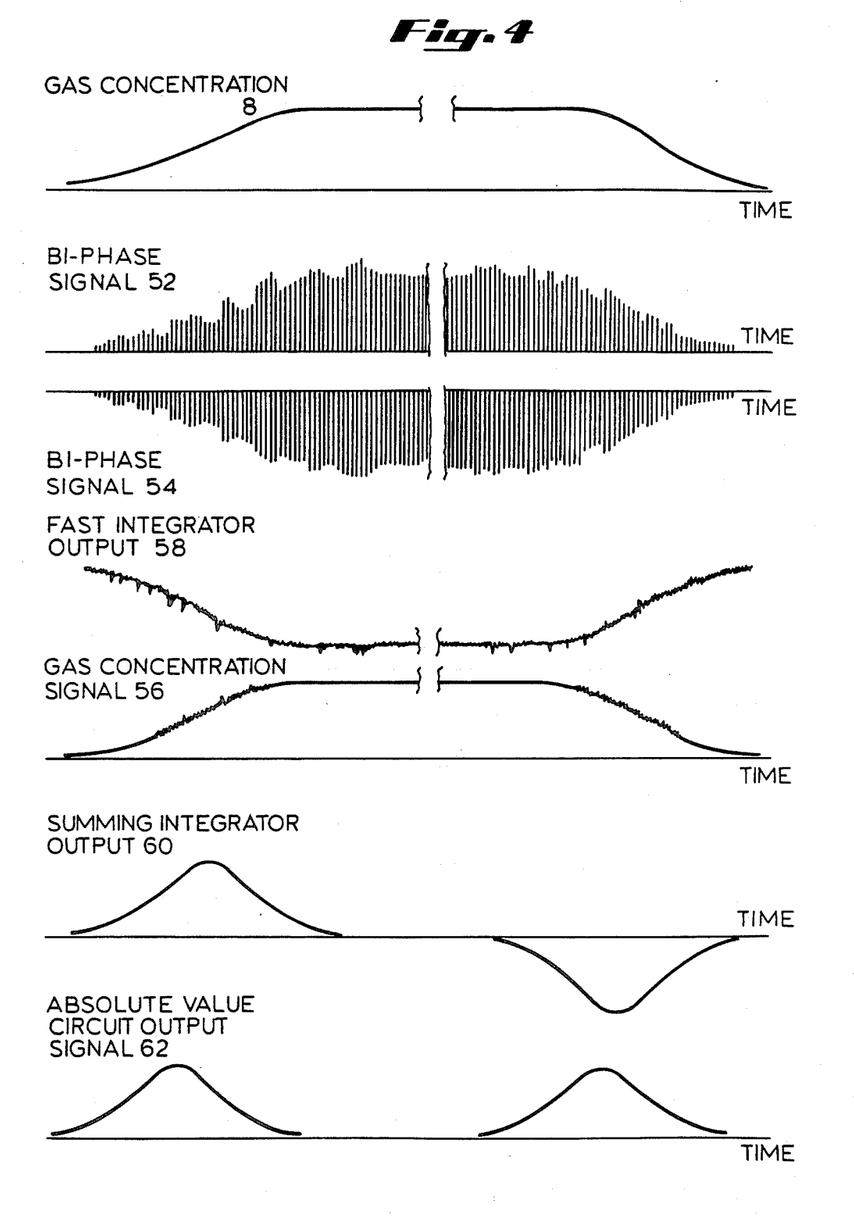
FIG. 4 shows waveforms seen in the signal processor during operation.

Referring now to FIG. 4, a graph 8 of changing gas concentration is plotted on a time axis together with plots of bi-phase signals 52 and 54, fast integrator output signal 58, gas concentration signal 56, summing integrator output signal 60 and absolute value circuit output signal 62. It may be seen that bi-phase signals 52 and 54 are trains of amplitude modulated pulses contaminated with noise. Apart from the noise contamination, bi-phase signals 52 and 54 are electrical inversions of each other, and each has an envelope generally proportional to the gas concentration graph 8. Signal 58 rises and falls more rapidly than signal 56 but has a greater noise content. Signal 60, the integrated sum of signals 56 and 58, is seen to be positive during gas concentration increases and negative during gas concentration decreases. Signal 62, the absolute value of signal 60, is a non-negative signal having its greatest amplitude during greatest changes in the gas concentration.

Figure 5:
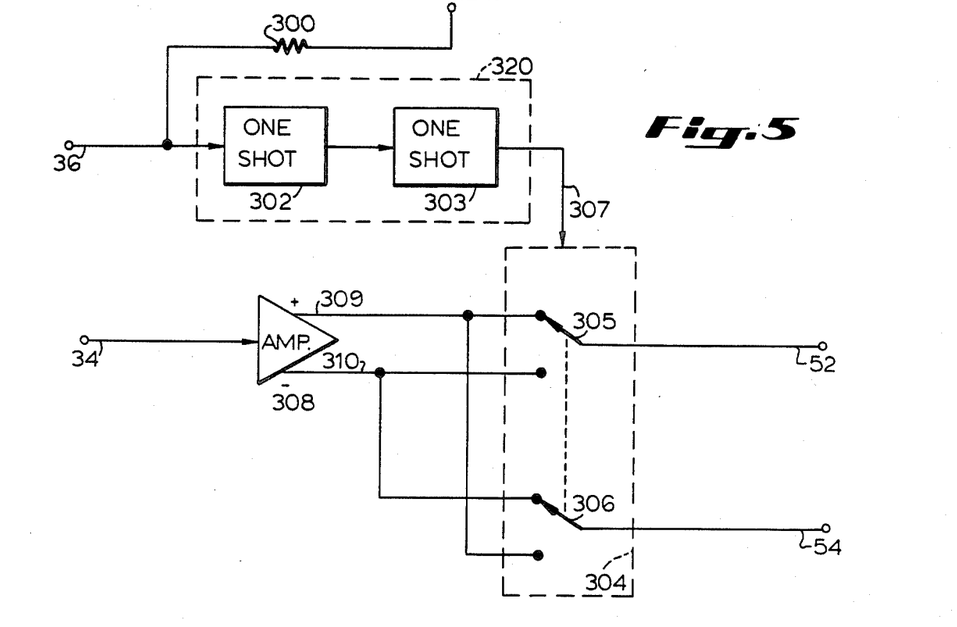
FIG. 5 shows the synchronous demodulator.

Examples of embodiments of the subsystem blocks shown in FIG. 3 are more particularly disclosed in FIGS. 5, 6, 7, and 8. Referring now to FIG. 5, the gas detection output signal 34 is conducted into amplifier 308. Amplifier 308 produces an amplified version of signal 34 at noninverting output 309 and inverting output 310. The signals produced at outputs 309 and 310 are identical except that they are electrical inversions of each other. Outputs 309 and 310 are conducted into electronic switch 304 to produce bi-phase signals 52 and 54.

Synchronous switch 304 is preferably an electronic microcircuit of a type exemplified by the RCA type CD4052B analog switch and will switch contacts 305 and 306 responsive to switch control signal 307. The components designated 302 and 303 are circuits well known in the electronic are variously as monostable multivibrators or "one shots." These one shots cooperate to produce signal 307 responsive to photodiode output signal 36.

One shots 302 and 303 comprises phase correcting circuit 320 and respond to an input electrical pulse by producing an output pulse of preselected duration. The duration of the output pulses of one shots 302 and 303 is preselected to produce a signal 307 which will switch contacts 305 and 306 responsive to signal 36. Specifically, contacts 305 and 306 must be switched to the position shown in FIG. 5 during the time that chopper 16 allows beams 11 and 13 to pass. The alternate position is taken by contacts 305 and 306 during the time chopper 16 interrupts the beams 11 and 13.

Figure 6:
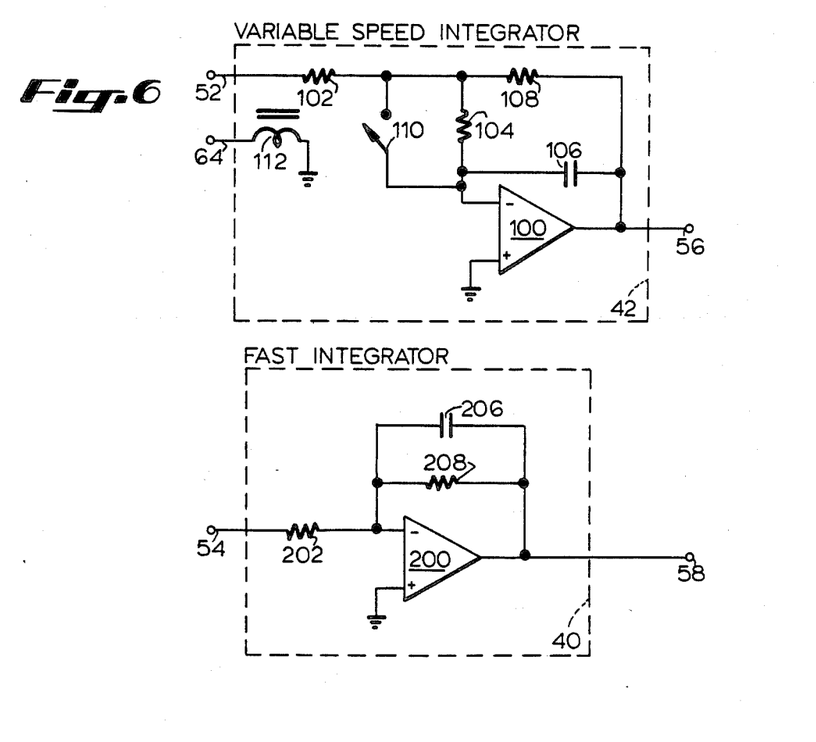
FIG. 6 shows the variable speed integrator and the fast integrator.

Referring now to FIG. 6, the fast integrator 40 and the variable speed integrator 42 are shown side by side for comparison. Fast integrator 40 is implemented using a high gain operational amplifier 200 cooperating with resistors 202 and 208 and capacitor 206 in a manner well known in the electronic art to form an integrator circuit. The time constant of integrator 40 is equal to the product of the resistance of resistor 208 and the capacitance of capacitor 206. The low frequency gain of integrator 40 is equal to the resistance of resistor 208 divided by the resistance of resistor 202.

High gain operational amplifier 100 similarly cooperates with resistors 102, 104 and 108, and capacitor 106 to form variable speed integrator 42. The low frequency gain of integrator 42 is equal to the resistance of resistor 108 divided by the resistance of resistor 102. The time constant of integrator 42 is adjusted to have either a long or short time constant responsive to whether relay contacts 110 are open or closed. When time constant control signal 64 is energized, current flows through relay solenoid 112 causing relay contacts 110 to close. De-energizing signal 64 causes the relay contacts 110 to open.

When contacts 110 are open, the time constant of integrator 42 is equal to the capacitance of capacitor 106 multiplied by the sum of the resistances of resistors 104 and 108. Closure of contacts 110 removes the resistor 104 from the circuit and reduces the time constant to the product of the capacitance of capacitor 106 and the resistance of resistor 108. The low frequency gain of integrator 42 is not affected by the opening or closing of contacts 110.

The values of the resistors and capacitors are preferably chosen to allow capacitor 206 and 106 to be identical. Similarly, resistors 202 and 102 are made identical and resistors 208 and 108 are made identical. Resistor 104 is then chosen so as to set the longer time constant of integrator 42. With these selections, both integrators will have the same low frequency gain and the fixed time constant of integrator 40 will be equal to the short time constant of variable speed integrator 42.

Figure 7:
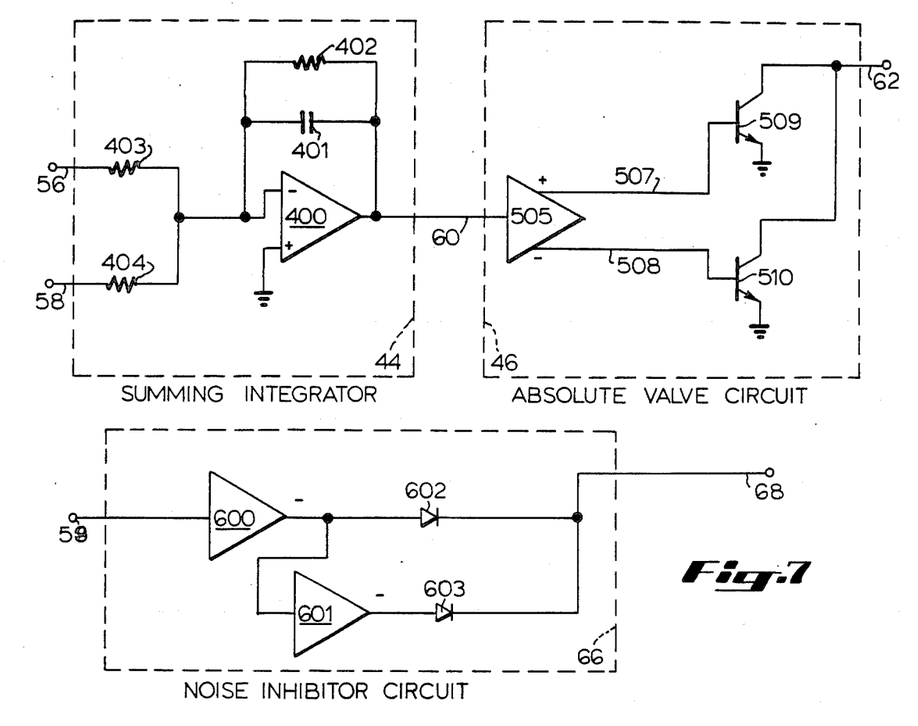
FIG. 7 shows the summing integrator, the absolute value circuit and the noise inhibitor circuit.

Referring now to FIG. 7, summing integrator 44 is shown in cooperation with absolute value circuit 46. The additive circuit comprising resistors 403 and 404, together with resistor 402 and capacitor 401, cooperate with high gain amplifier 400 to produce an integrator circuit in a manner well known in the electronic art as previously disclosed. In absolute value circuit 46, amplifier 505 produces noninverting output 507 and inverting output 508 in a manner similar to that of amplifier 308 in FIG. 5. Transistors 509 and 510 are combined in a configuration known in the electronic art as "push pull-parallel" to produce output signal 62. Noise inhibitor circuit 66 comprises inverting amplifier 600 and inverting amplifier 601 cooperating with diodes 602 and 603 to produce output signal 68.

Figure 8:
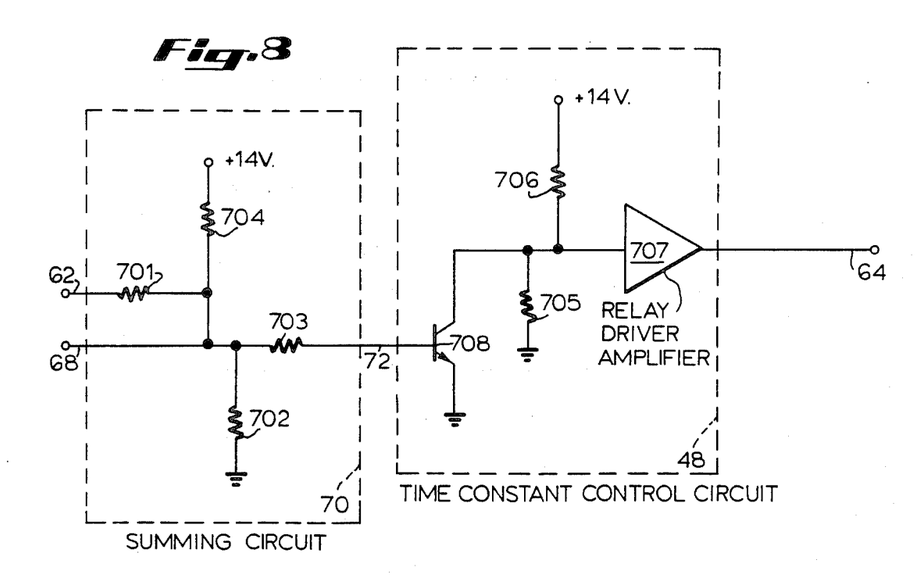
FIG. 8 shows the summing circuit and the time constant control circuit.

Referring now to FIG. 8, output signal 62, from absolute value circuit 46, and output signal 68, from noise inhibitor circuit 66, are additively combined in summing circuit 70. The presence of high noise input to the system will result in a positive voltage contribution by signal 68, causing signal 72 to be at a higher positive voltage. Transistor 708 will thus be in a high conducting state and will reduce the input to relay driver amplifier 707. A change in gas concentration will cause signal 72 to be at a lower positive voltage, resulting in a lower conducting state of transistor 708. Responsive to the lower conducting state of transistor 708, relay driver amplifier 707 will produce a positive voltage on signal 64 suitable to energize relay solenoid 112 in FIG. 6.

Analysis and experimentation has shown that suitable values of time constant for gas detection in an oilfield drilling environment are approximately the following:

Variable speed integrator 42 long time constant: 74.5 seconds

Variable speed integrator 42 short time constant: 7.05 seconds

Fast integrator 40 time constant: 7.05 seconds.

The longer value of time constant permits sufficient filtering out of vibration induced noise during periods when gas concentration remains relatively unchanged for many hours at a time. The shorter value of time constant permits the variable speed integrator to respond to faster gas concentration changes, which may occur in less than one minute. Also, selection of 7.05 seconds for the shorter time constant permits the variable speed integrrator to respond sufficiently rapidly during calibration of the signal processor. Operation in environments other than oilfield drilling may dictate other suitable values.

A suitable value of time constant for the summing integrator has been found by experimentation and analysis to be approximately 14.1 seconds. This value of time constant permits sufficiently fast response of the summing integrator 44 without passing excessive noise to the absolute value circuit 46. As previosly disclosed, gas measurement in environments other than oilfield drilling may dictate other values. The choice of a time constant for summing integrator 44 will depend on the nature of the noise encountered in the particular environment in which gas concentration is measured.

The low frequency gains of the fast integrator 40 and the variable speed integrator 42, as well as the gain of amplifier 308, are dictated by the amplitude of the signal 34. Signal 34 is usually of the order of a few millivolts for practical embodiments of the Luft detector. Experimentation and analysis has shown that a gain of approximately 200 for amplifier 308, and a value of approximately 1.4 for the low frequency gains of the fast integrator 40 and the variable speed integrator 42, provide sufficient amplification based on the amplitude range encountered for signal 34.

The foregoing description of an embodiment of the invention should be considered illustrative of the invention but not limiting. This invention is directed to any and all alternative embodiments which are obvious to one skilled in the art and the invention is limited only by the claims which follow.

I claim:

1. In a gas analyzer using a twin beam infrared absorption gas detector comprised of a reference chamber filled with a sample of a reference gas, a sample chamber partitioned into a first detection zone and a second detection zone by a flexible diaphragm, the flexible diaphragm being deformably responsive to a pressure differential between the first detection zone and the second detection zone, the first and second detection zones being filled with a sample of the reference gas, a first source of infrared energy for directing a first infrared beam through the reference chamber into the first detection zone, a second infrared source for directing a second infrared beam through the sample chamber into the second detection zone, and output circuitry adapted to produce an output signal substantially proportional to the deformation of the diaphragm, the improved signal processor comprising:
   (a) a variable speed integrator having an output and adapted to produce a signal substantially proportional to the concentration of the reference gas in the sample chamber, the variable speed integrator having an adjustable time constant;
   (b) circuitry adapted to adjust the time constant of the variable speed integrator responsive to the rate of change of the output signal substantially proportional to the deformation of the diaphragm; and
   (c) display means adapted to display the signal produced at the output of the variable speed integrator as the concentration of the reference gas in the sample chamber.

2. The signal processor of claim 1, further comprising:
   (a) an optical chopper adapted to periodically interrupt the first and second infrared beams directed by the first and second sources of infrared energy, the periodic interruption being at a preselected frequency; and
   (b) a synchronous demodulator adapted to synchronously demodulate the output signal which is substantially proportional to the deformation of the diaphragm, the demodulation occurring in synchronism with the preselected frequency of the optical chopper, an output of the demodulator comprising an input to the variable speed integrator.

3. The signal processor of claim 2, wherein the preselected frequency is wobulated.

4. The signal processor of claim 1 or claim 2, wherein the variable speed integrator has a time constant which may be switchably adjusted to assume one of two preselected values.

5. The signal processor of claim 4 wherein the circuitry adapted to adjust the time constant of the variable speed integrator comprises:
   (a) a fast integrator having an output and adapted to integrate the output signal substantially proportional to the deformation of the diaphragm; and
   (b) circuitry adapted to compare the respective rates of change of the outputs of the variable speed integrator and the fast integrator.

6. The signal processor of claim 5, wherein the fast integrator has a low frequency gain which is substantially equal to the low frequency gain of the variable speed integrator.

7. The signal processor of claim 4, wherein the ratio of the two preselected values of time constant is approximately 10.

8. The signal processor of claim 4, wherein the two values of the time constant of the variable speed integrator are substantially 7.05 seconds and substantially 74.5 seconds.

9. The signal processor of claim 4, wherein the variable speed integrator has a low frequency gain which remains substantially constant as the time constant of the variable speed integrator is adjusted.

10. In a gas analyzer using a twin beam infrared absorption gas detector comprised of a reference chamber filled with a sample of a reference gas, a sample chamber filled with an unknown gas mixture, a detection chamber partitioned into a first detection zone and a second detection zone by a flexible metal diaphragm, the diaphragm being deformably responsive to a pressure differential between the two detection zones, the two detection zones being filled with a sample of the reference gas, a first infrared source for directing a first infrared beam through the reference chamber into the first detection zone, a second infrared source for directing a second infrared beam through the sample chamber into the second detection zone, a rotating optical chopper adapted to interrupting the infrared beam at a frequency of substantially 10 Hertz, a fixed metal plate spaced closely to the diaphragm so as to form a variable capacitor responsive to the deformation of diaphragm, and a power supply adapted to supply a direct current voltage to the variable capacitor so formed so as to produce an electrical signal responsive to capacitance variations in the variable capacitor, the improved signal processor comprising:

(a) a synchronous demodulator comprising an electronic amplifier adapted to amplify the electrical signal responsive to the capacitance variations of the variable capacitor with a gain of about 200 and producing an inverting output signal and a non-inverting output signal, and a synchronous switch responsive to a synchronous control signal so as to sample the non-inverting output signal of the electronic amplifier to produce a first bi-phase output signal and further to sample the inverting output signal of the electronic amplifier so as to produce a second bi-phase signal;

(b) a variable speed integrator adapted to filter the first bi-phase output signal, the variable speed integrator having a time constant switchably selectable so as to assume either a value of substantially 7.05 seconds or a value of substantially 74.5 seconds, the variable speed integrator having a low frequency gain of substantially 1.4 irrespective of the time constant value selected;

(c) a fast integrator adapted to filter the second bi-phase output signal, the fast integrator having a time constant of substantially 7.05 seconds, the fast integrator having a low frequency gain of substantially 1.4;

(d) a summing integrator adapted to produce an output signal substantially equal to the filtered difference of the output signal of the variable speed integrator and the output signal of the fast integrator, the summing integrator having a time constant of substantially 14.1 seconds;

(e) an absolute value circuit adapted to produce an output signal substantially equal to the absolute value of the output signal of the summing integrator;

(f) a noise inhibitor circuit adapted to produce an output signal substantially equal to the absolute value of the output signal of the fast integrator;

(g) a time constant control circuit adapted to select the time constant of the variable speed integrator responsive to the difference between the output signal of the absolute value circuit and the output signal of the noise inhibitor circuit; and (h) display means suitably calibrated to display the output signal of the variable speed integrator as the concentration of the reference gas in the unknown gas mixture.

11. A method of detecting the concentration of a reference gas in an unknown gas mixture using a twin beam infrared absorption gas detector having a capacitor comprising a diaphragm deformably responsive to the concentration and a plate spaced closely thereto comprising the steps of:

(a) producing a voltage substantially proportional to the deformation of the diaphragm;

(b) integrating the voltage in a variable speed integrator having an adjustable time constant to produce a signal substantially proportional to the concentration; and (c) adjusting the time constant of the variable speed integrator such that the time constant is made relatively long during periods in which the concentration remains relatively unchanging and made relatively short during the periods in which the concentration is substantially increasing or substantially decreasing.

12. The method of claim 11 wherein producing the voltage substantially proportional to the deformation of the diaphragm further comprises the steps of:

(a) periodically chopping the twin beams at a preselected frequency; and (b) synchronously demodulating a voltage across the capacitor to produce the voltage substantially proportional to the deformation of the diaphragm.

13. The method of claim 12, further comprising the step of wobulating the preselected frequency.

14. The method of claim 11, further comprising the steps of holding the low frequency gain of the variable speed integrator constant.

15. A method of detection of a reference gas in an unknown gas mixture using a twin beam infrared gas detector producing an output voltage substantially proportional to the concentration of the reference gas in the unknown mixture but containing substantial amounts of noise, comprising the steps of:

(a) periodically chopping the twin infrared beams with an optical chopper at preselected frequency;

(b) synchronously demodulating the output voltage of the gas detector in synchronism with the preselected frequency to produce a first bi-phase output signal and a second bi-phase output signal;

(c) integrating first bi-phase output signal with a variable speed integrator having an adjustable time constant;

(d) integrating the second bi-phase output signal in a fast integrator having a fixed time constant;

(e) combining and integrating the output signals of the fast integrator and the variable speed integrator to produce a time constant control signal;

(f) adjusting the time constant of the variable speed integrator responsive to the time constant control signal; and (g) displaying the output signal of the variable speed integrator as the concentration of the reference gas.

* * * * *

UNITED STATES PATENT AND TRADEMARK OFFICE
CERTIFICATE OF CORRECTION

PATENT NO. : 4,694,174
DATED : September 15, 1987
INVENTOR(S) : Louis W. Erath

It is certified that error appears in the above-identified patent and that said Letters Patent are hereby corrected as shown below:

Column 1, line 16, delete "gasses" and insert --gases--.

Column 1, line 25, delete "permeates" and insert --permeate--.

Column 1, line 37, delete "gasses" and insert --gases--.

Column 1, line 43, delete "gasses" and insert --gases--.

Column 1, line 48, delete "gasses" and insert --gases--.

Column 2, line 9, delete "Gasses" and insert --Gases--.

Column 5, line 3, delete "remidied" and insert --remedied--.

Column 6, line 8, delete "lights" and insert --light--.

Column 6, line 15, delete "references" and insert --reference--.

Column 7, line 68, delete "are" and insert --art--.

Column 8, line 4, delete "comprises" and insert --comprise--.

Column 9, line 33, delete "integrrator" and insert
   --integrator--.

UNITED STATES PATENT AND TRADEMARK OFFICE
CERTIFICATE OF CORRECTION

PATENT NO. : 4,694,174

DATED : September 15, 1987

INVENTOR(S) : Louis W. Erath

It is certified that error appears in the above-identified patent and that said Letters Patent is hereby corrected as shown below:

Column 10, line 1, before "partitioned", insert --filled with an unknown gas mixture, a detection chamber--.

Signed and Sealed this

Thirty-first Day of May, 1988

Attest:

Attesting Officer

DONALD J. QUIGG

Commissioner of Patents and Trademarks